United States Patent [19]

Kozak

[11] 4,036,233

[45] July 19, 1977

[54] FLEXIBLE WAIST DIAPER

[75] Inventor: Theodore Fredrick Kozak, Manchester, Conn.

[73] Assignee: Union Carbide Corporation, New York, N.Y.

[21] Appl. No.: 702,220

[22] Filed: July 2, 1976

[51] Int. Cl.$^2$ .................. A41B 13/02; A61F 13/16
[52] U.S. Cl. .................. 128/287; 128/290 R; 128/296
[58] Field of Search .......... 128/284, 286, 287, 290 R, 128/296

[56] References Cited

U.S. PATENT DOCUMENTS

| | | |
|---|---|---|
| 2,931,361 | 4/1960 | Sostrin .................. 128/284 |
| 3,344,789 | 10/1967 | Arnold .................. 128/287 |
| 3,586,000 | 6/1971 | Ness .................. 128/287 |
| 3,828,784 | 8/1974 | Zoephel .................. 128/287 |
| 3,886,941 | 6/1975 | Duane .................. 128/287 |
| 3,890,974 | 6/1975 | Kozak .................. 128/287 |
| 3,920,018 | 11/1975 | Schaar .................. 128/287 |
| 3,951,151 | 4/1976 | Teed .................. 128/287 |

Primary Examiner—Aldrich F. Medbery
Attorney, Agent, or Firm—Clement J. Vicari

[57] ABSTRACT

A disposable diaper having a topsheet and backsheet one of which is stretchable, the other non-stretchable and wherein both extend beyond the edges of the absorbent material to provide a waistband. The non-stretchable sheet is provided with openings to permit stretching of the waistband.

19 Claims, 4 Drawing Figures

FLEXIBLE WAIST DIAPER

This invention relates to disposable diapers and more particularly relates to a disposable diaper which is provided with a reinforced stretchable waistband formed from the topsheet and backsheet of the disposable diaper.

The use of disposable diapers has greatly increased in recent years due to their ease of use, low cost and the obvious sanitary value of having a clean, fresh, disposable diaper for use without the inconvenience of having to wash and reuse a previously used nondisposable diaper.

In its most fundamental construction a disposable diaper merely comprises a layer of disposable absorbent material lining a backing sheet of liquid impermeable material which may be disposable or reusable. The thickness of the layer of absorbent material can be varied depending upon the desired use. For example, if the diaper were to be used overnight for an older baby it would be required to have a greater absorptive capacity than one used for a short time during the day or for an infant and consequently the absorbent layer would be thicker. The length and width of the diaper can also be varied for different size babies. Generally, the absorbent pad will be about ⅛ to ½ inch thick and the diaper will have a length of about 12 to 18 inches and a width of about 8 to 16 inches.

While a baby diaper constructed in this manner supplies the essential ingredients of a disposable diaper, namely an absorbent layer and a liquid impermeable backing sheet, modifications have previously been proposed to overcome one or more of the defects inherent in the basic construction. It was found, for example, that when the absorbent layer became soaked with urine it tended to wad together or lost most of its integral strength and began to shred.

In order to overcome these disadvantages it has been common to place a layer of non-woven gauze, or other material which will maintain its integrity after wetting on top of the absorbent layer of the diaper thereby sandwiching the absorbent layer between a topsheet of self-supporting but liquid permeable material and a backing sheet of liquid impermeable material. Such a construction overcame the disadvantages of shredding but tended to make the baby uncomfortable after wetting since the urine would partially be absorbed by the topsheet which was against the skin of the baby. This contact of the baby's skin with urine on the surface of the diaper is one of the principal causes of diaper-derived skin rash. Additionally, upon removal of a wet diaper, it was found that the baby's skin was wet and drying was necessary before a clean diaper could be applied.

In an attempt to overcome this deficiency it has been suggested that the topsheet be made hydrophobic or water-shedding to maintain the layer which is in contact with the baby's skin as dry as possible. One recognized approach has been to form the topsheet of the diaper in part or completely of hydrophobic fibers or by coating or impregnating an otherwise hydrophilic topsheet with a hydrophobic resin.

In another recognized approach, a film of plastic has been utilized as the topsheet of the diaper with provision being made for the passage of liquid through the plastic topsheet into the absorbent pad.

Thus according to U.S. Pat. No. 3,814,101 issued June 4, 1974, the plastic topsheet for the disposable diaper described therein is provided with valvular openings for passage of liquid therethrough to the absorbent core. U.S. Pat. No. 3,221,738 issued to G. E. Eckberg et al. on Dec. 7, 1965 discloses as topsheet for a disposable diaper, a thin plastic foil which is heat treated in such a way that the liquid insulating property of the foil is completely or partially neutralized, so that liquid reaching the heat-treated foil surface is automatically sucked in through the foil and absorbed by the core. More recently U.S. Pat. No. 3,929,135 issued to Hugh Ansley Thompson on Dec. 30, 1975 provides a plastic topsheet for a disposable diaper having tapered capillaries of specific design and construction and which is adapted to pass liquid therethrough into an absorbent layer disposed subjacent to the topsheet.

It has been the custom to secure these disposable diapers on an infant by utilizing a pressure sensitive tape fastener which has been disposed on the backsheet of the diaper in an area overlying the absorbent pad. When the disposable diaper is placed on an infant the tape fastener is secured to either abutting or overlapping corners of the diaper as to provide as secure a fit as possible around the waist of an infant. Since the waist size of infants can vary appreciably it has heretofore been difficult to provide a proper fit for the diaper which would be both comfortable to the infant while at the same time providing safeguards against leakage through the top of the diaper particularly when the infant is in a prone position. This is because of the construction of conventional diapers which have not afforded any appreciable expansive properties when tapes were fastened to the diapers and applied to the infant. Neither tape nor waist construction of conventional diapers has any significant "give" or resiliency and in fact efforts have been made to make the tape fastener and the area accommodating the tape fastener relatively strong and relatively ungiving. This unyielding characteristic makes it difficult to maintain good fit during the rigors of usage.

According to the present invention it has been found that the above disadvantages can be either eliminated or reduced significantly by appropriate selection of materials of specific construction for the topsheet and backing sheet coupled with appropriate positioning of the tape fasteners on a disposable diaper.

Accordingly it is an object of the present invention to provide a disposable diaper having a stretchable waistband.

A further object of the invention is to provide a topsheet and backsheet for a disposable diaper one of which is stretchable as described herein and wherein both topsheet and backsheet extend beyond the absorbent pad in the diaper length direction and which when bonded together at the extended sites form a waistband for the diaper.

A further object is to provide a disposable diaper in which the waistband of the diaper can be stretched to a greater degree than the body or core of the diaper which accommodates the absorbent material therein.

A further object is to provide a reinforced stretchable waistband for a disposable diaper fabricated from the topsheet and backsheet of the diaper and wherein either the topsheet or backsheet imparts the stretchable characteristics of the waistband while the other serves to reinforce the waistband.

A still further object is to provide a stretchable waistband for a disposable diaper which is fabricated from a stretchable material bonded to a non-stretchable material and wherein openings are provided in the non-stretchable material to permit stretching of the stretchable material.

These and other objects will be apparent from the following description taken in conjunction with the accompanying drawings in which:

FIG. 1 is a perspective view of a diaper with a portion cut away to reveal details of construction and which is made in accordance with the present invention having a backsheet of non-stretchable material and a topsheet and wherein the topsheet is fabricated from a stretchable water impermeable plastic material provided with openings for passage of liquid and showing the topsheet extending beyond the longitudinal edges of the absorbent pad and adhered to extended portions of the backsheet to form a waistband for the diaper.

Figure 1:
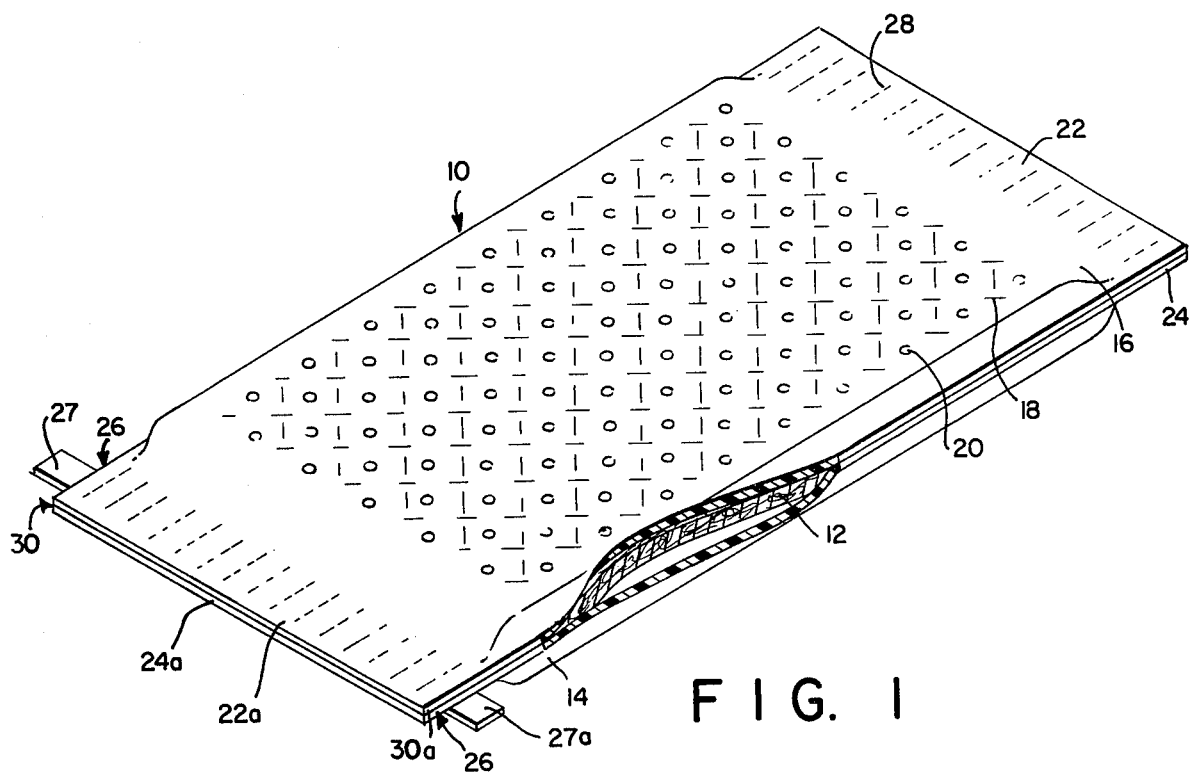

Broadly contemplated, the present invention provides a disposable diaper having a stretchable waistband comprising in combination a topsheet for placement adjacent to the body and being provided with means for passing liquid therethrough, a water impermeable backsheet and an absorbent pad disposed between said topsheet and backsheet, one of said topsheet or backsheet being a stretchable plastic film having a Young's Modulus of less than 5000 lbs/in$^2$, preferably from 300 to 4000 lbs/in$^2$ and most preferably from 350 to 1000 lbs/in$^2$ and which exhibits recovery of characteristics such that at up to 20% elongation it will recover about 99% and from 20 to 50% elongation it will recover from about 99 to 90% respectively and still maintain a force of not less than 0.05 lbs, preferably not less than 0.3 lbs, the other of said topsheet or backsheet being fabricated from a non-stretchable material, said topsheet and backsheet having end portions extending beyond said absorbent pad in diaper length direction, said stretchable plastic film constituting said topsheet or backsheet being adhered to said non-stretchable material in said end portions to form a reinforced stretchable waistband for said diaper, said non-stretchable material in said end portion being provided with openings in an amount and frequency such as to permit effective stretching of said waistband. Fastening means such as a pair of pressure sensitive tape fasteners each having a fixed and segment secured to a corner of the waistband of the diaper on one of the end portions of the diaper is also provided.

In my copending application Ser. No. 702,211 filed concurrently herewith and assigned to a common assignee, there is disclosed a stretchable waistband for a disposable diaper which is fabricated from either the topsheet or backsheet of a disposable diaper one of which is stretchable and extends beyond the absorbent pad and which when folded upon itself forms the stretchable waistband for the diaper. The non-stretchable sheet is substantially shorter in length in the diaper length direction than the stretchable sheet and is adhered to the stretchable sheet at a point proximate the absorbent pad edge.

According to the present invention, the topsheet and backsheet are of substantially equal length and extend beyond the longitudinal edges (diaper length direction) of the absorbent pad a distance sufficient to form a waistband for the diaper. Either the backsheet or topsheet is a stretchable (as defined herein) water impermeable hydrophobic film of plastic material, whereas the other film which is non-stretchable, i.e., it does not have the stretch properties as defined above, is bonded to the stretchable film in the waistband region, and acts as a reinforcement of the waistband. The non-stretchable film in the waistband portion is provided with an arrangement of openings or slits in the diaper length direction which are of a length and frequency such as not to interfere with the effective widthwise stretching of the waistband.

In the copending application of Theodore F. Kozak and Paul Mohr, Ser. No. 702,212 filed concurrently herewith and assigned to a common assignee, there is disclosed a stretchable plastic film material suitable for use as an outer covering for a disposable diaper.

The stretchable plastic film disclosed therein are suitable for use in the present invention and therefore the disclosure of copending application Ser. No. 702,212 is incorporated herein by reference.

Briefly however, the stretchable plastic film contemplated for use in the present invention is critical and is limited to those materials possessing the required strength and stretchability. The material should be thin, flexible, self-supporting, and substantially a water impermeable sheet of film.

It is essential that the stretchable plastic film contemplated for use in the present invention be one having the requisite stress to strain properties as determined at any specified point.

Thus the film must have a stretch (Young's) modulus less than 5000 lbs./in$^2$, and must also exhibit recovery such that at up to 20% elongation it will recover 99% and from 20 to 50% elongation it will recover from 99% to 90% and still maintain a force of 0.05 lbs.

Examples of stretchable hydrophobic films having the requisite properties include films of ethylene-ethyl acrylate, having the requisite ethylacrylate content, ethylene vinyl acetate, polyvinyl chloride, and films made from polyester urethanes such as "Estane" 5710 resin available from B. F. Goodrich Co.

Films fabricated from polyethylene would not be suitable since they do not meet the above criteria. However copolymers of ethylene could be suitable provided the polymer content is controlled so as to conform to the above criteria.

Figure 2:
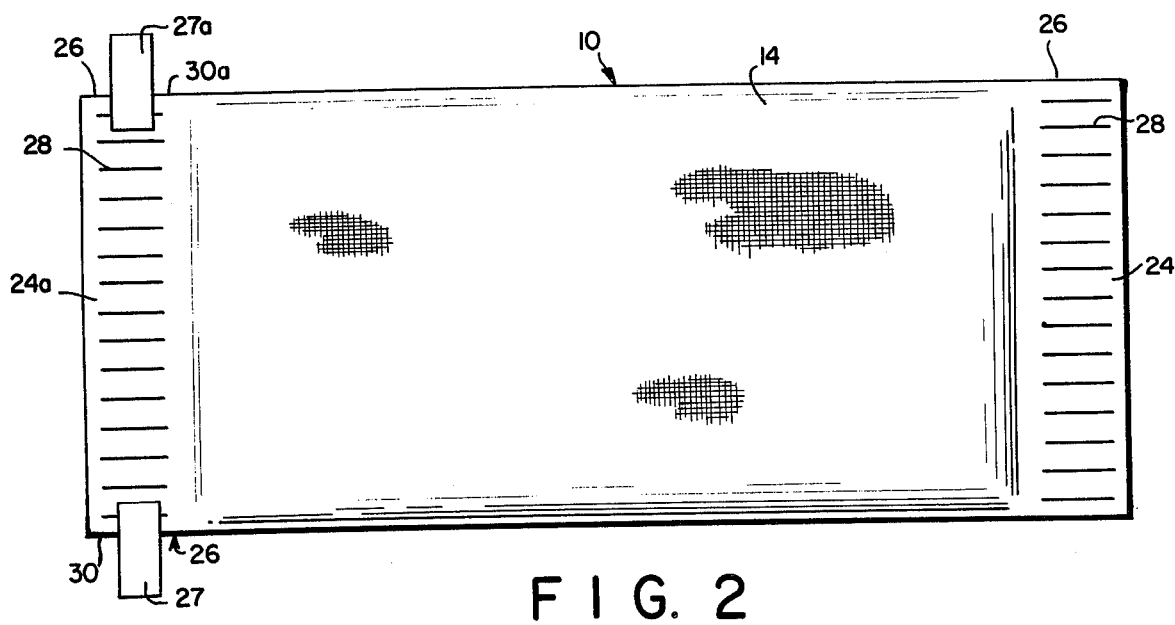
FIG. 2 is a view looking towards the backsheet of the diaper which shows the openings in the extended portions of the backsheet which permits effective widthwise stretching of the stretchable topsheet and wherein the backsheet which is adhered to the topsheet at the extended portions also serves to reinforce the extended portions of the topsheet to provide a reinforced waistband for the diaper.

For a clearer understanding of the invention reference is made to FIGS. 1 and 2 which illustrates the preferred embodiment of the invention and wherein reference numeral 10 generally designates the disposable diaper of the instant invention.

The diaper 10 includes a rectangular absorbent pad 12 substantially centrally located and sandwiched between a thin, flexible backsheet 14 of liquid impermeable material such as polyethylene film and a thin stretchable (as defined herein) plastic topsheet 16 also of a normally liquid impermeable material. Topsheet 16 is provided with means for passing liquid to the absorbent pad such as is disclosed in U.S. Pat. No. 3,221,738 or U.S. Pat. No. 3,929,135. Preferably however, topsheet 16 has a plurality of valvular openings 18 and can include a system of dimples 20 as disclosed in U.S. Pat. No. 3,814,101.

The absorbent pad 12 can be a plurality of layers of absorbent tissue paper or wadding stacked to the desired thickness. The wadding layers need not be adhered to each other but, since it has been common practice to adhesively, mechanically, or otherwise secure the layers to each other to maintain the relative position of the layers and the shape of the absorbent pad, such can also be done in the disposable diaper of the present invention. The wadding can be stacked to form a pad of any desired thickness and hence absorbency can be controlled for any particular use.

Absorbent materials other than tissue and wadding will of course be useful in the diaper construction of the present invention. For example, absorbent non-woven pads can be fabricated to any desired thickness and substituted for the absorbent pads described above. One such absorbent pad which has been used extensively in disposable diapers is a wood pulp product commonly known as wood fluff and is prepared in the same manner as a non-woven fabric. Thus such type absorbent pad is also useful as the absorbent pads of the inserts of the present invention.

The only criteria for utility in the present invention are that the material be absorbent, be capable of being fabricated in the form of a pad, be compatible with the waste products with which it will come in contact and be non-irritating to the skin.

As mentioned previously, the material used in the fabrication of the topsheet 16 of the diaper illustrated in FIGS. 1 and 2 is critical and is limited to those materials possessing the required strength and stretchability.

As shown in FIG. 1 topsheet 16 extends longitudinally beyond the absorbent pad 12 to form end portions 22 and 22a.

These end portions each extend longitudinally in the diaper length direction beyond absorbent pad 12 and transversely across the diaper 10.

Backsheet 14 is preferably an olefinic or vinyl film. Polyethylene of a thickness of from about 0.4 to about 1.5 mils is most preferred. This type of film has previously been used extensively for this purpose and commonly has had an embossed design in its surface to simulate the appearance and hand of cloth. These manufacturing techniques will also find use in the diaper of the present invention. As shown in FIG. 2, the backsheet extends longitudinally beyond the absorbent pad 12 to form end portions 24, 24a which are adhered to extended end portions 22, 22a of topsheet 16 to form waistband 26. In the case where both the backsheet 14 and topsheet 16 are fabricated from thermoplastic materials, the adhesion can be effected by heat sealing, otherwise other conventional adhering techniques can be utilized as is well known to those skilled in the art. The end portions 22, 22a and 24, 24a when adhered together constitute the waistband 26 of the diaper and since one of the materials constituting the waistband is stretchable (topsheet 16) and the other material non-stretchable (backsheet 14) it will be obvious that the degree of stretching of the waistband is limited by the stretchability of the backsheet. This can be overcome by providing an arrangement of vertical openings or slots 28 in the backsheet in the area of the waistband of the diaper. Thus referring to FIG. 2, it will be seen that openings are provided in the end portions 24, 24a of backsheet 14 which are of a length and frequency which will permit stretching of the waistband an amount depending on the stretchability of the stretchable topsheet 16. In general, the openings can be curvilinear, or straight, and can be formed by either a cutting action wherein no material is removed from the backsheet (which is preferred according to the present invention), or on the other hand, the vertical openings can be formed by removal of material from the backsheet to form spaced openings. The length of the vertical openings depends in part on the length (the distance in diaper length direction) of the waistband. The waistband can be of a length of ¾ to 2 inches preferably 1¼ to 1½ inches. In general the length of the vertical openings can be varied over a relatively wide range such as from about 20 to 75% of the length of the waistband. For optimum effect, the vertical openings are substantially centrally evenly spaced between the opposing ends of the waistband in the diaper length direction. The number of openings depends on the dimensions of the diaper employed. As a general rule, the amount or frequency of the vertical openings should be such that the stretching of the waistband is in effect controlled by the stretchability of the stretchable material constituting the topsheet of the diaper.

The waistband 26 extends from absorbent pad 12 a distance sufficient to accommodate a fastening means such as a pair of tape fasteners 27 and 27a on the corners 30 and 30a of waistband 26, (although it will be obvious that the tape fasteners can alternately be positioned on the other corners of the waistband. It will be seen that where the tape fasteners 27 and 27a are positioned on corners 30 and 30a that the area is free of absorbent pad material and indeed the entire waistband 26 is free of absorbent pad material.

Figure 3:
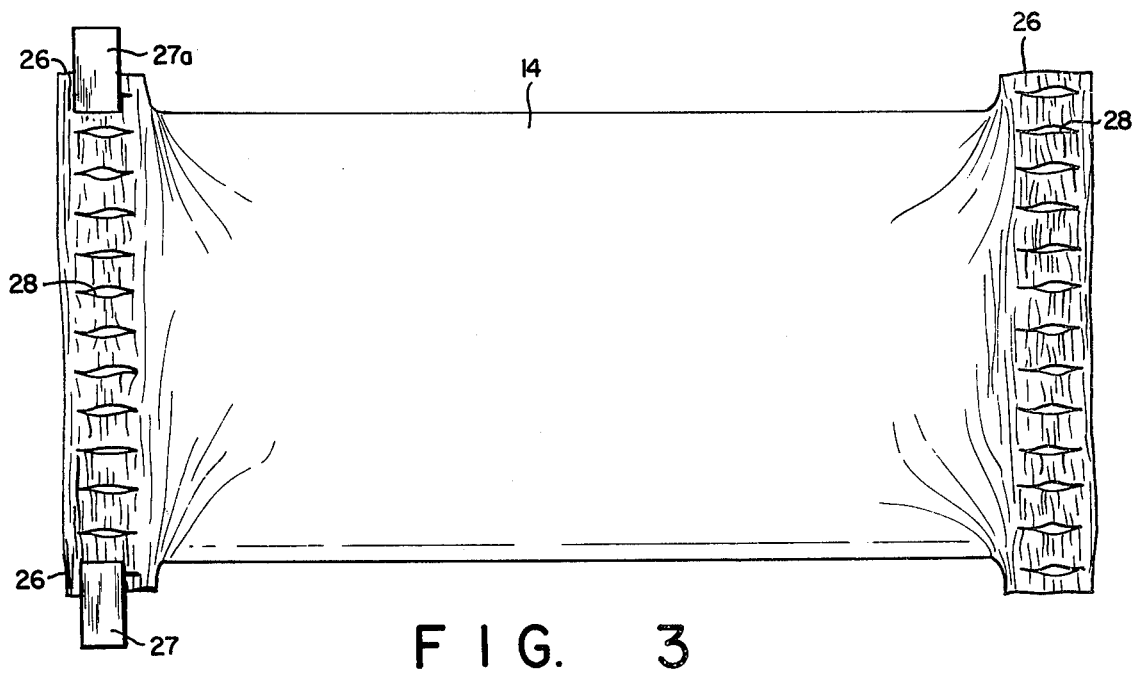
FIG. 3 is similar to FIG. 2 but showing the waistband in a stretched condition.

FIG. 3 shows the diaper of FIG. 2 in stretched condition i.e., the waistband stretched and the openings 28 extended.

Conventionally, it has been the practice to adhere the absorbent pad to the backsheet or topsheet. Thus under conventional techniques when the tape fastener was secured to the backsheet it was positioned overlying the absorbent material. Exerting pressure on the tape fastener to accommodate a large waist size infant resulted in tearing of the backsheet and/or separation of the absorbent material due to the non-yieldability of the structure.

According to the present invention the tape fasteners are positioned on the waistband 26 so that no absorbent material underlies the tape fastener. Since the topsheet is stretchable, and since the waistband is an extension of the backsheet and topsheet body material, pressure can be exerted on the tape fastener when mounting the diaper on the infant so that the greatest amount of stress is placed on the waistband portion of the diaper which has a higher permissible degree of stretchability than the backsheet and topsheet overlying the absorbent material which is normally adhered to the absorbent material to prevent migration of the absorbent material.

One film which has been found particularly useful as the topsheet is an ethylene-ethyl acrylate film having the properties mentioned previously. The film should have a thickness of from about 0.4 to about 2.0 mils with about 1.0 to 1.5 mils being preferred.

As described above, the topsheet 16 is provided with means for permitting passage of liquid therethrough and is also optionally provided with dimples 20.

According to the preferred embodiment illustrated in FIGS. 1 and 2 the means for passing liquid are valvular openings or slits and the dimples on the top surface of the diaper are of a construction and frequency as disclosed in U.S. Pat. No. 3,803,101 the disclosure of which is incorporated herein by reference. Briefly however, and as disclosed in the above mentioned patent the term "valvular" as used throughout the specification and in the claims is intended to refer to apertures in the top surface which are capable of opening to permit passage of liquid under certain circumstances and reclosing to retard passage of liquid under certain other circumstances. When open, the valvular openings should have the ability to pass at least 20 milliliters of liquid within 10 seconds when an area of about 20 square inches is wetted.

The assembly of the diaper follows, more or less, conventional methods of fabrication. The topsheet and backsheet are cut to approximately the same dimensions. The size can be varied according to the desired use, for example in an infant's diaper a size of 10 × 16 inches for the backsheet and the topsheet might be sufficient whereas in a diaper for a large child a size of 12 × 18 inches for the backsheet and the topsheet would be better and a size of 14 × 20 inches for the backsheet and the topsheet might be preferred for a diaper which could accommodate a toddler.

The topsheet and backing sheet are juxtaposed one on the other with the absorbent pad sandwiched therebetween in approximately the center of the sheets. The absorbent pad should be of a width smaller than the backsheet to permit sealing of the topsheet to the backing sheet around their sides. An overhang of about one-half inch on each side should be sufficient. Sealing can conveniently be accomplished by heat sealing the side edges.

Figure 4:
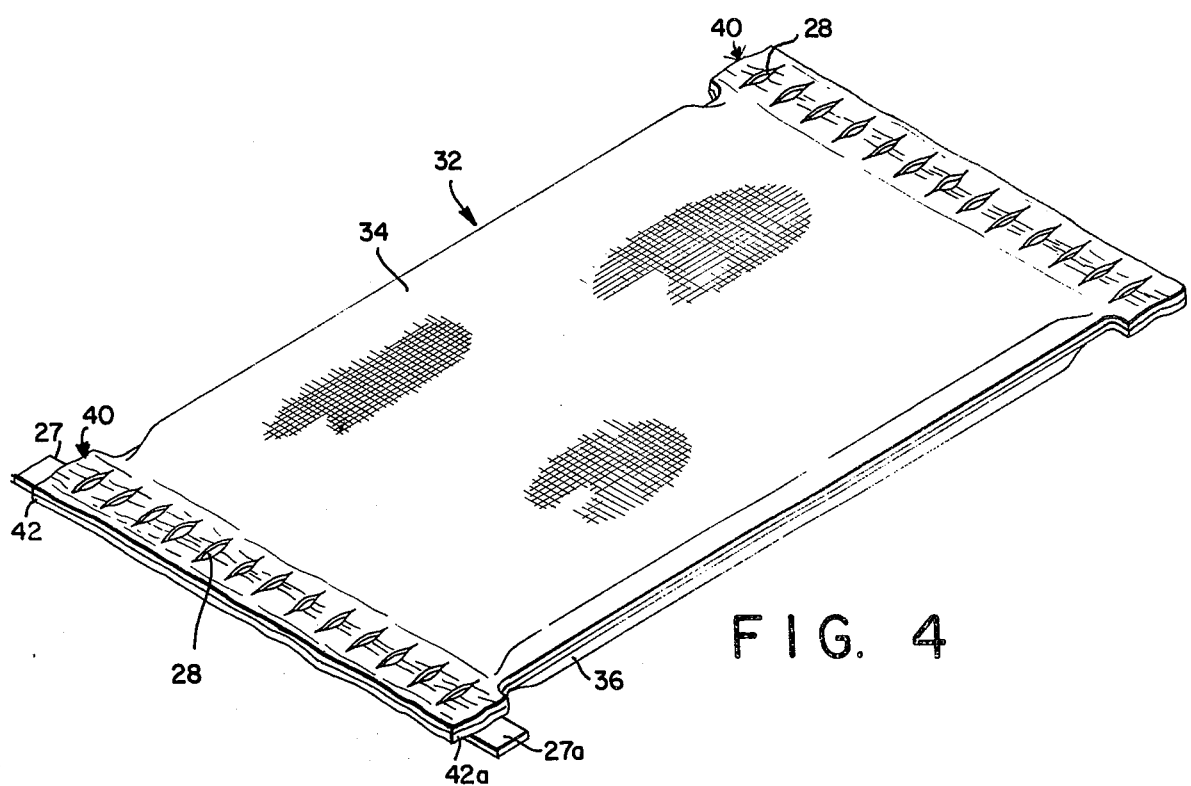
FIG. 4 is a view similar to FIG. 1 wherein the backsheet is fabricated from a stretchable material and wherein the topsheet is non-stretchable and provided with openings in the waistband portion and which shows the waistband in stretched position.

According to another embodiment of the invention, illustrated in FIG. 4 where like parts are indicated by like reference numbers, the stretchable waistband shown in stretched condition is formed from the backsheet of the disposable diaper. Thus referring to FIG. 4 the diaper 32 includes the absorbent pad sandwiched between a liquid permeable topsheet 34 and a thin stretchable plastic backsheet 36 of liquid impermeable material.

Topsheet 34 can be a porous non-woven material and can be composed in part or completely of hydrophobic fibers. Alternatively, the topsheet can be hydrophilic and treated with a hydrophobic resin such as by coating or impregnating the otherwise hydrophilic topsheet with the hydrophobic resin. The backsheet 36 is constructed of the same materials as the topsheet 16 of the preferred embodiment of diaper 10 shown in FIGS. 1 and 2 and has end portions of the topsheet and backsheet which are adhered to form waistband 40.

Openings or slots 28 are provided in the topsheet which serve the same function and are of the character as the openings depicted in FIG. 1.

Fastening means 27, 27a are disposed on the corner portions 42 and 42a of the waistband 40 to secure the diaper to the infant.

Although the fastening means illustrated in both embodiments are tape fasteners, it will be obvious that other conventional fastening means known to the art can be utilized.

The type of tape fastener which can be utilized is conventional in the art and in general contains a fixed end segment which is permanently affixed to the diaper and a releasable end segment having some form of adhesion on its surface and which is adapted to be adhesively secured to opposing corners of the diaper.

The materials used in the fabrication of the tape fastener of the present invention are not limited to any particular chemical composition since it is their physical properties rather than their chemical properties which are important according to the invention. These materials should, of course, be less flexible than the materials of the topsheet and backsheet and should be self-supporting.

Merely as illustrative, the pressure sensitive tape fasteners disclosed in U.S. Pat. Nos. 3,853,129 and 3,874,386 issued Dec. 10, 1974 and Apr. 1, 1975 respectively can be utilized.

It will be obvious that while the present invention has been set forth in some detail and described with particularity it is susceptible to changes, modifications and alterations without departing from the scope and spirit of the invention as defined in the appended claims.

What is claimed is:

1. A disposable diaper having a stretchable waistband comprising in combination, a topsheet for placement adjacent to the body and being provided with means for passing liquid therethrough, a water impermeable backsheet and an absorbent pad disposed between said topsheet and backsheet, one of said topsheet or backsheet being a stretchable plastic film having a Young's Modulus of less than 5000 lbs/in$^2$ and which exhibits recovery characteristics such that at up to 20% elongation it will recover about 99% and from 20 to 50% elongation it will recover from 99 to 90% respectively and still maintain a force of not less than 0.05 lbs, the other of said topsheet or backsheet being fabricated from a non-stretchable material, said topsheet and backsheet having end portions extending beyond said absorbent pad in diaper length direction, said stretchable plastic film constituting said topsheet or backsheet being adhered to said non-stretchable material in said end portions to form a reinforced stretchable waistband for said diaper, said non-stretchable material in said end portion being provided with openings in an amount and frequency such as to permit effective stretching of said waistband, and fastening means secured to opposing corners of said waistband on one of the end portions of said diaper.

2. A disposable diaper according to claim 1 wherein said fastening means are pressure sensitive tape fasteners each having a fixed end and a releasable end and wherein said fixed end is secured to a corner of said waistband of the diaper on one of the end portions of said diaper.

3. A disposable diaper according to claim 2 wherein said topsheet is fabricated from said plastic film material and wherein said backsheet is fabricated from said non-stretchable material and wherein said openings in said end portion are vertical openings disposed between opposing ends of said waistband in the diaper length direction.

4. A disposable diaper according to claim 3 wherein said backsheet is a polyethylene film.

5. A disposable diaper according to claim 4 wherein said means for passing liquid through said topsheet are valvular openings and wherein said topsheet also includes a system of dimples extending across the surface of said topsheet.

6. A disposable diaper according to claim 1 wherein said plastic film has a Young's modulus of from 300 to 4000 lbs/in$^2$.

7. A disposable diaper according to claim 1 wherein said plastic film has a Young's modulus of from 350 to 1000 lbs/in$^2$.

8. A disposable diaper according to claim 7 wherein said plastic film is an ethylene-ethyl acrylate film.

9. A disposable diaper according to claim 8 wherein said ethylene-ethyl acrylate film has a thickness of from about 0.4 to about 2.0 mils.

10. A disposable diaper according to claim 1 wherein said waistband is from ¾ to 2 inches in length.

11. A disposable diaper according to claim 1 wherein said waistband is from 1¼ to 1½ inches in length.

12. A disposable diaper according to claim 2 wherein said backsheet is fabricated from said plastic film material and wherein said topsheet is fabricated from said non-stretchable material and wherein said openings are vertical openings disposed between opposing ends of said waistband in the diaper length direction.

13. A disposable diaper according to claim 12 wherein said topsheet is a polyethylene film.

14. A disposable diaper according to claim 12 wherein said topsheet is fabricated from non woven cloth.

15. A disposable diaper according to claim 12 wherein said plastic film has a Young's modulus of from 300 to 4000 lbs/in$^2$.

16. A disposable diaper according to claim 12 wherein said plastic film has a young's modulus of from 350 to 1000 lbs/in$^2$.

17. A disposable diaper according to claim 12 wherein said plastic film is an ethylene-ethyl acrylate film.

18. A disposable diaper according to claim 12 wherein said waistband is from ¾ to 2 inches in length.

19. A disposable diaper according to claim 12 wherein said waistband is from 1¼ to 1½ inches in length.

* * * * *